United States Patent [19]

Stoltefuss et al.

[11] Patent Number: 4,645,775

[45] Date of Patent: Feb. 24, 1987

[54] POSITIVE INOTROPIC 3-NITRO-5-SUBSTITUTED ESTER AND THIOESTER-1,4-DIHYDROPYRIDINES

[75] Inventors: Jürgen Stoltefuss, Haan; Fred R. Heiker; Gerhard Franckowiak, both of Wuppertal; Matthias Schramm, Cologne; Günter Thomas; Rainer Gross, both of Wuppertal, all of Fed. Rep. of Germany

[73] Assignee: Bayer Aktiengesellschaft, Leverkusen, Fed. Rep. of Germany

[21] Appl. No.: 734,502

[22] Filed: May 15, 1985

[30] Foreign Application Priority Data

Jun. 4, 1984 [DE] Fed. Rep. of Germany ....... 3420784

[51] Int. Cl.[4] ................. C07D 211/90; C07D 401/12; C07D 413/04; A61K 31/455
[52] U.S. Cl. .................................... 514/352; 546/310; 546/271; 546/272; 514/338; 514/339
[58] Field of Search ....................... 546/310, 271, 272; 514/352, 338, 339

[56] References Cited

U.S. PATENT DOCUMENTS 4,248,873  2/1981  Bossert et al. ...................... 546/304
4,532,248  7/1985  Franckowiak et al. ............. 514/302

Primary Examiner—Henry R. Jiles
Assistant Examiner—Dale A. Bjorkman
Attorney, Agent, or Firm—Sprung Horn Kramer & Woods

[57] ABSTRACT

Novel 3-nitro-dihydropyridine derivatives of the formula

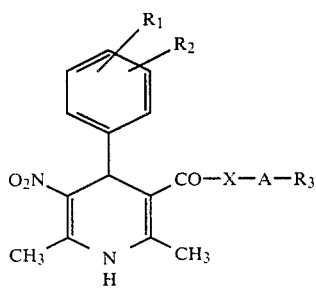

in which $R_1$ and $R_2$ each independently is hydrogen, $C_1$-$C_4$-alkyl, $C_1$-$C_{12}$-alkoxy, $C_1$-$C_4$-halogenoalkoxy, halogen, nitro, $C_1$-$C_4$-halogenoalkyl, $C_1$-$C_4$-halogenoalkylmercapto,

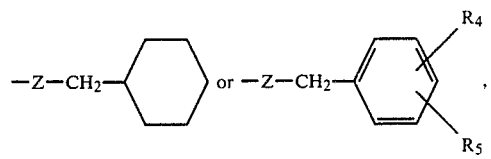

Z is oxygen or sulphur, $R_4$ and $R_5$ each independently is hydrogen, $C_1$-$C_4$-alkyl, $C_1$-$C_6$-alkoxy, halogen, $C_1$-$C_4$-halogenoalkyl, $C_1$-$C_4$-halogenoalkoxy or nitro, or $R_1$ and $R_2$, together with 2 C atoms of the phenyl ring form the ring

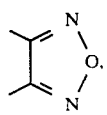

X is oxygen or sulphur, A is a hydrocarbon radical with up to 12 C atoms which optionally contains one or two identical or different chain members from the group comprising O, S and CO and/or which is optionally substituted by hydroxyl or aliphatic acyloxy with up to 4 C atoms, $R_3$ is —O—$COR_6$, —S—CO—$R_6$, SH, OH, $NH_2$,

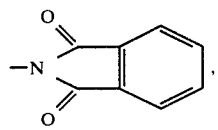

NH—$COR_6$, $COOR_6$, $NR_7R_8$ or $CONR_7R_8$, $R_6$ is hydrogen or an aliphatic radical with up to 6 C atoms or a phenyl radical, and $R_7$ and $R_8$ each independently is hydrogen or an aliphatic radical with up to 6 C atoms or a phenyl radical, or a physiologically acceptable salts thereof, which are active in circulation and exhibit positive inotropic activity.

9 Claims, No Drawings

POSITIVE INOTROPIC 3-NITRO-5-SUBSTITUTED ESTER AND THIOESTER-1,4-DIHYDROPYRIDINES

The present invention relates to new 3-nitrodihydropyridines, processes for their preparation and their use in medicaments, in particular in medicaments which have an influence on the circulation and have a positively inotropic action.

It has already been disclosed that 1,4-dihydropyridines have vasodilating properties and can be used as coronary agents and antihypertensives (compare British Patent Specification No. 1,173,062; British Patent Specification No. 1,358,951; DE-OS (German Published Specification) No. 2,629,892 and DE-OS (German Published Specification) No. 2,752,820). It is furthermore known that, as calcium antagonists, 1,4-dihydropyridines inhibit the contraction force of smooth and cardiac muscle and can be used for the treatment of coronary and vascular diseases (compare A. Fleckenstein, Ann. Rev. Pharmacol. Toxicol. 17, 149–166 (1977)).

Knowing these properties of the dihydropyridines, it was not to be predicted that the compounds from this class of substance which are mentioned below have no contraction-inhibiting action but have a contraction force-intensifying action which is positively inotropic on the cardiac muscle.

The present invention relates to new 3-nitrodihydropyridine derivatives of the general formula (I)

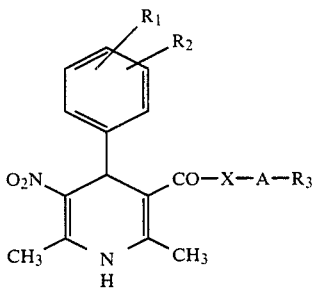

in which $R_1$ and $R_2$ can be identical or different and represent hydrogen, $C_1$-$C_4$-alkyl, $C_1$-$C_{12}$-alkoxy, $C_1$-$C_4$-halogenoalkoxy, halogen, nitro, $C_1$-$C_4$-halogenoalkyl, $C_1$-$C_4$-halogenoalkylmercapto or one of the groups

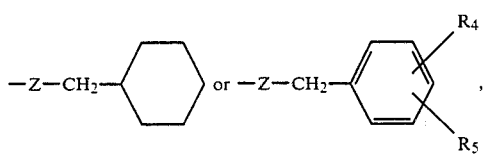

in which

Z denotes oxygen or sulphur and $R_4$ and $R_5$ can be identical or different and denote hydrogen, $C_1$-$C_4$-alkyl, $C_1$-$C_6$-alkoxy, halogen, $C_1$-$C_4$-halogenoalkyl, $C_1$-$C_4$-halogenoalkoxy or nitro, or $R_1$ and $R_2$, together with 2 C atoms of the phenyl ring, form the ring

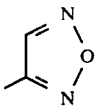

X denotes oxygen or sulphur,

A represents a straight-chain or branched, saturated or unsaturated hydrocarbon radical with up to 12 C atoms, which optionally contains one or two identical or different chain members from the group comprising O, S and CO, and/or which is optionally substituted by hydroxyl or aliphatic acyloxy with up to 4 C atoms, and $R_3$ represents a radical from the group comprising —O—$COR_6$, —S—CO—$R_6$, SH, OH, $NH_2$,

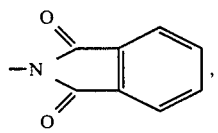

NH—$COR_6$, $COOR_6$, $NR_7R_8$ and $CONR_7R_8$ wherein $R_6$ denotes hydrogen or an aliphatic radical with up to 6 C atoms or a phenyl radical and $R_7$ and $R_8$ denote hydrogen or an aliphatic radical with up to 6 C atoms or a phenyl radical, and physiologically acceptable salts thereof.

Preferred compounds of the formula (I) are those in which $R_1$ represents hydrogen, $R_2$ represents halogen, trifluoromethyl, nitro, hydrogen, $C_1$-$C_4$-alkyl or one of the groups

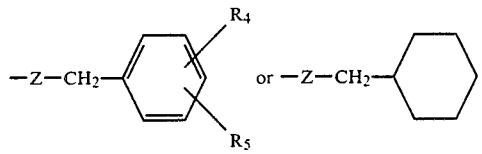

wherein

Z, $R_4$ and $R_5$ have the meanings already given, $R_3$ represents $OCOR_6$, S—$COR_6$, SH, $NH_2$, $COOR_6$, NH—$COR_6$ or —CO—$NR_7R_8$, X denotes oxygen or sulphur, A represents a $C_2$-$C_8$-alkyl group, and $R_6$, $R_7$ and $R_8$ denote a $C_1$-$C_3$-alkyl radical, and physiologically acceptable salts thereof.

Particularly preferred compounds of the formula (I) are those in which $R_1$ represents hydrogen, $R_2$ represents halogen, trifluoromethyl, nitro, hydrogen or one of the groups

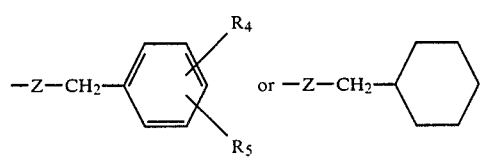

wherein

Z, $R_4$ and $R_5$ have the meanings already given, $R_3$ represents $OCOR_6$, S—$COR_6$ or SH, X denotes oxygen or sulphur, A represents a $C_2$-$C_8$-alkyl group, and $R_6$ denotes a $C_1$-$C_3$-alkyl radical.

The dihydropyridines of the general formula (I) according to the invention can be prepared by a process in which (A) aminocrotonic acid esters of the general formula (II)

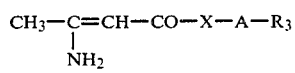

in which X, A and $R_3$ have the abovementioned meaning, are reacted with aldehydes of the general formula (III)

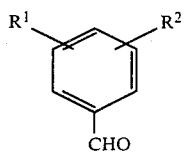

in which $R_1$ and $R_2$ have the abovementioned meaning, and nitroacetone of the formula $$CH_3-CO-CH_2-NO_2$$

or (B) benzaldehydes of the formula (III) and acetoacetic acid esters of the general formula (IV)

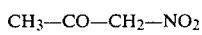

in which X, A and $R_3$ have the abovementioned meaning, or Knoevenagel condensation products thereof (ylidene compounds) of the general formula (V)

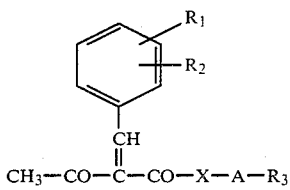

are reacted with an addition compound of nitroacetone and ammonia, of the formula

or (C) by a process in which aminocrotonic acid esters of the formula (II) are reacted with benzylidene-nitroacetones of the general formula (VI)

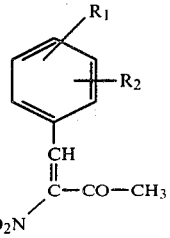

or (D) by a process in which carboxylic acid derivatives of the general formula

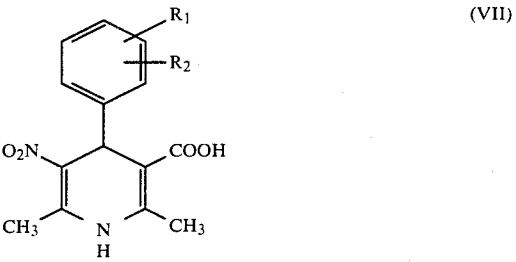

are reacted with compounds of the general formula (VIII)

$$H-X-A-R_3 \qquad (VIII)$$

in which X, A and $R_3$ have the abovementioned meaning, by known methods, if appropriate via a reactive acid derivative, or (E) by a process in which compounds of the formula I in which $R_1$, $R_2$, X and A have the abovementioned meaning and $R_3$ represents —$OCOR_6$, —S—$COR_6$ or —NH—$COR_6$, are converted into compounds of the formula I in which $R_3$ represents OH, SH or —$NH_2$ by transesterification, or (F) by a process in which compounds in which $R_1$, $R_2$, X and A have the abovementioned meaning and $R_3$ represents OH, $NH_2$ or SH, are converted into compounds where $R_3$ is —O—$COR_6$, —NH—$COR_6$ or —S—$COR_6$ by acylation by known methods, or (G) to prepare compounds of the general formula I in which $R_1$, $R_2$, X and A have the abovementioned meaning and $R_3$ represents —S—$COR_6$ or —O—$COR_6$, by a process in which compounds of the general formula IX

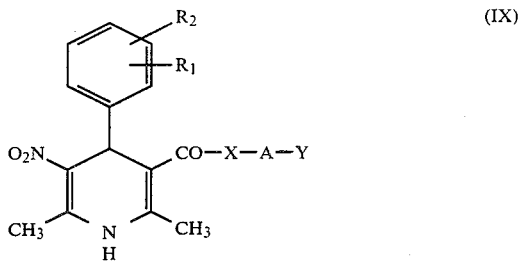

in which $R_1$, $R_2$, X and A have the abovementioned meaning and Y represents a halogen atom or a reactive group, such as, for example, a mesyl, tosyl or triflate group, are reacted with compounds of the general formula X MeR₃                                      (X)

in which

Me denotes a reactive metal atom, preferably an alkali metal atom, and $R_3$ represents —S—$COR_6$ or —O—$COR_6$.

If, for example, β-aminocrotonic acid esters and benzaldehyde are reacted with nitroacetone according to process variant (A), the reaction can be represented by the following equation:

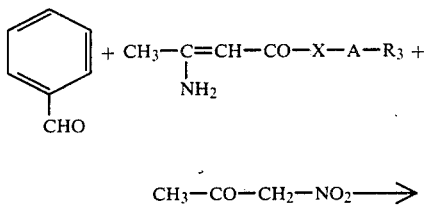

$CH_3$—CO—$CH_2$—$NO_2$ —→

[Structure: 1,4-dihydropyridine with phenyl, $O_2N$, $CH_3$, CO—X—A—$R_3$, $CH_3$, NH] + 2$H_2O$ If, for example, 2-trifluorobenzylidene-acetoacetic acid esters are reacted with nitroacetone/ammonia according to process variant (B), the reaction can be represented by the following equation:

[Structure: 2-CF₃-phenyl-CH=C(COCH₃)(COX—A—$R_3$)]

$CH_3$—CO—$CH_2$—$NO_2$.$NH_3$ —→

[Structure: 1,4-dihydropyridine with 2-CF₃-phenyl, $O_2N$, $CH_3$, COX—A—$R_3$, $CH_3$, NH] + 2$H_2O$ If, for example, 2-benzyloxybenzylidene-nitroacetone is reacted with aminocrotonic acid esters according to process variant (C), the reaction can be represented by the following equation:

[Structure: 2-benzyloxyphenyl-CH=C($NO_2$)(COCH₃)] +

$CH_3$—C(NH₂)=CH—COX—A—$R_3$ —→

[Structure: 1,4-dihydropyridine with 2-benzyloxyphenyl, $O_2N$, $CH_3$, COX—A—$R_3$, $CH_3$, NH] + $H_2O$ If, for example, β-bromoethyl 1,4-dihydro-2,6-dimethyl-3-nitro-4-(2-chlorophenyl)pyridine-5-carboxylate is reacted with potassium thioacetate according to process variant 6, the reaction can be represented by the following equation:

[Structure: 1,4-dihydropyridine with 2-Cl-phenyl, $O_2N$, $CH_3$, COO—$CH_2$—$CH_2$—Br, $CH_3$, NH] + KS—COCH₃ —→

[Structure: 1,4-dihydropyridine with 2-Cl-phenyl, $O_2N$, $CH_3$, COO—$CH_2$—$CH_2$—S—COCH₃, $CH_3$, NH] + KBr Possible diluents for all the process variants A and B to G are all the inert organic solvents. These include, preferably, alcohols, such as ethanol, methanol and isopropanol, ethers, such as dioxane, diethyl ether, tetrahydrofuran, glycol monomethyl ether and glycol dimethyl ether, or glacial acetic acid, dimethylformamide, dimethylsulphoxide, acetonitrile, pyridine and hexamethylphosphoric acid triamide.

The reaction temperatures can be varied within a substantial range. In general, the reaction is carried out between 10° and 150° C., in particular between 20° and 120° C., but preferably at the boiling point of the particular solvent.

The reaction can be carried out under normal pressure, but also under increased pressure. In general, the reaction is carried out under normal pressure.

The preparation processes above are given only for illustration, and the preparation of the compounds of the formula (I) is not restricted to these processes, but any modification of these processes can be applied in the same manner to the preparation of the compounds according to the invention.

The reactants can be used in any desired ratio to one another, and in general equimolar amounts are employed. However, it has proved advantageous to employ up to a 5 molar excess of the nitroacetone in process A and the nitroacetone/ammonia adduct in process B.

Depending on the choice of the starting substances, the compounds according to the invention can exist in stereoisomeric forms which either behave as mirror images (enantiomers) or do not behave as mirror images (diastereomers). The present invention relates both to the antipodes and to the racemic forms as well as the diastereomer mixtures. The racemic forms and the diastereomers can be separated into the stereoisomerically uniform constituents in a known manner (compare, for example, E.L. Eiliel, Stereochemistry of Carbon Compounds, McGraw Hill, 1962).

The aminocrotonic acid esters of the formula (II) are known in some cases, or they can be prepared by known methods from acetoacetic acid esters of the formula (IV) with ammonia, compare A. C. Cope, J. Am. Chem. Soc. 67, 1017 (1945).

The acetoacetic acid esters of the formula (IV) are known in some cases, or they can be prepared by methods which are known per se (compare D. Borrmann, "Umsetzung von Diketen mit Alkoholen, Phenolen und Mercaptanen" ("Reaction of diketene with alcohols, phenols and mercaptans"), in Houben-weyl, Methoden der organischen Chemie (Methods of Organic Chemistry), Vol. VII/4, 230 et seq. (1968); and Y. Oikawa, K. Sugano and O. Yonemitsu, J. Org. Chem. 43, 2087 (1978)).

The aldehydes (III) used are known or can be prepared by methods which are known from the literature (compare T. D. Harris and G. P. Roth, J. org. Chem. 44, 146 (1979); German Offenlegungsschrift (German Published Specification) No. 2,165,260; German Offenlegungsschrift (German Published Specification) No. 2,401,665; Mijano et al., Chem. Abstr. 59 (1963), 13 929 c; E. Adler and H.-D. Becker, Chem. Scand. 15, 849 (1961); and E. P. Papadopoulos, M. Mardin and Ch. Issidoridis, J. Org. Chem. 31, 615 (1966), J. Am. chem. Soc. 78, 2543 (1956)).

The ylidene compounds of the formula (V) which can be used according to the invention are not known, but they can be prepared by known methods [Organic Reactions XV, 204 et seq. (1967)].

The compounds of the formula (VI) which can be employed are known and are described in H. Dornoff and W. Sassenberg, Liebigs Ann. Chem. 602, 14 (1957).

The nitroacetone $\times NH_3$ addition product can be prepared by a method analogous to that according to H. Böhme and K.-H. Weise Arch. Pharm., 310, 30 (1977).

Nitroacetone can be prepared by known methods (compare N. Levy and C. W. Scarfe, J. Chem. Soc (London) (1946) 1103; and C. D. Hurd and M. E. Nilson, J. Org. Chem. 20, 927 (1955)).

The compounds of the formulas VII to X are already known or can be prepared by known methods, compare European Published Application 71,819.

The new active compounds can be converted in a known manner into the customary formulations, such as tablets, capsules, dragees, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which suffice to achieve the dosage range mentioned.

The formulations are prepared, for example, by extending the active compounds with solvents and/or excipients, optionally with the use of emulsifiers and/or dispersing agents, and, for example, when using water as the diluent, organic solvents can optionally be used as auxiliary solvents.

Examples of auxiliary substances which may be mentioned are: water, non-toxic organic solvents, such as paraffins (for example petroleum fractions), vegetable oils (for example groundnut/sesame oil), alcohols (for example ethyl alcohol and glycerol) and glycols (for example propylene glycol and polyethylene glycol), solid carriers, such as, for example, natural rock powders (for example kaolins, aluminas, talc and chalk), synthetic rock powders (for example highly disperse silica and silicates) and sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium lauryl-sulphate).

Administration is effected in the customary manner, preferably orally or parenterally, in particular perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl-sulphate and talc, can be co-used when making tablets. In the case of aqueous suspensions and/or elixirs which are intended for oral use, the active compounds can be mixed with various flavor-improving agents or colorants, in addition to the abovementioned auxiliary substances.

In the case of parenteral use, solutions of the active compounds are preferably employed, using suitable liquid excipients.

In general, it has proved advantageous to administer amounts of about 0.001 to 1 mg/kg of body weight, preferably about 0.01 to 0.5 mg/kg of body weight, to achieve effective results in the case of intravenous administration, and in the case of oral administration the dosage is about 0.01 to 20 mg/kg, preferably 0.1 to 10 mg/kg.

Nevertheless, it can at times be necessary to deviate from the amounts mentioned, and in particular to do so as a function of the body weight of the experimental animal or of the nature of the administration route, but also because of the animal species and its individual behavior towards the medicament or the nature of the formulation of the medicament and the time or interval over which the administration takes place. Thus, it can suffice in some cases to manage with less than the abovementioned minimum amount, whilst in other cases the upper limit mentioned must be exceeded. Where relatively large amounts are administered, it may be advisable to divide these into several individual administrations over the course of the day. The same dosage range is envisaged for administration in human medicine. The general sense of the above statements also applies here.

The compounds according to the invention have a positive inotropic action and thus exhibit a useful pharmacological action spectrum which cannot be predicted. They can be used as cardiotonics to improve the contractility of the heart. Moreover, they can be employed as antihypertensives, for reducing blood sugar, for reducing swelling of mucous membranes and for influencing the salt and fluid balance.

The positively inotropic action of the compounds of the formula (I) according to the invention is determined in the following experimental design; those compounds which already exhibit a positively inotropic action on the left auricle of the isolated guinea-pig heart from a concentration of $10^{-5}$ g/ml are to be particularly preferred here:

The left auricles of guinea-pig hearts are isolated and suspended in a thermostatically controlled organ bath containing an isotonic mineral salt solution, which matches the ionic medium and the pH value of body fluids, with suitable nutrients. This organ bath is gassed with a gas mixture consisting of oxygen and carbon dioxide, the carbon dioxide content being chosen so that the pH value of the organ bath remains constant. The left auricles are clamped in the organ bath and the tension is recorded by means of a force transducer, a certain base tonus being established. The left auricles are then electrically stimulated continuously at certain intervals and the contractions which thereby take place are recorded. After addition of the active compound, recording of the contractions is continued. An intensification of contractions of at least 25% is regarded as a significant positively inotropic action.

Thus, for example, the contractions of the left guinea-pig auricle stimulated electrically with 1 Hz are intensified by 65% by $10^{-5}$ g/ml of the compound from Example 28 and by 94% by the compound from Example 34.

EMBODIMENT EXAMPLES

EXAMPLE 1

(Process variant A)

β-Acetoxyethyl 1,4-dihydro-2,6-dimethyl-3-nitro-4-(2-chlorophenyl)-pyridine-5-carboxylate

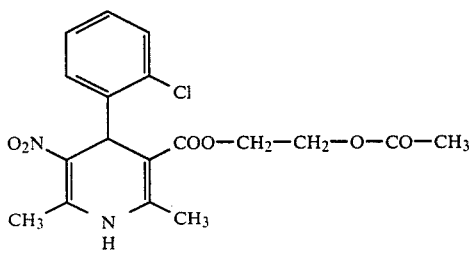

28.1 g (200 mmol) of 2-chlorobenzaldehyde are boiled under reflux with 37.4 g (200 mmol) of 2-acetoxyethyl β-aminocrotonate and 32.6 g (320 mmol) of nitroacetone in 400 ml of ethanol for 4 hours. The mixture is cooled and concentrated. The evaporation residue is taken up in ethyl acetate and the mixture is washed with water, sodium bicarbonate solution and water again, dried and concentrated. The semi-solid evaporation residue is stirred with ethanol, filtered off with suction and washed with ethanol. 23.2 g (29.4% of theory) of a yellow-colored product of melting point 158°–160° C. are obtained.

The following compounds are prepared analogously:

EXAMPLE 2

β-Acetoxyethyl 1,4-dihydro-2,6-dimethyl-3-nitro-4-(2-benzyloxy-phenyl)-pyridine-5-carboxylate of melting point 199° C.

EXAMPLE 3

β-Acetoxyethyl 1,4-dihydro-2,6-dimethyl-3-nitro-4-phenylpyridine-5-carboxylate of melting point 163°–165° C.

EXAMPLE 4

2-Acetylthioethyl 1,4-dihydro-2,6-dimethyl-3-nitro-4-(2-benzyloxy-phenyl)-pyridine-5-carboxylate of melting point 152°–154° C.

EXAMPLE 5

3-Acetylthio-propyl 1,5-dihydro-2,6-dimethyl-3-nitro-4-(2-benzyloxy-phenyl)-pyridine-5-carboxylate of melting point 185°–187° C.

EXAMPLE 6

β-Phthalimido-ethyl 1,4-dihydro-2,6-dimethyl-3-nitro-4-(2-benzyloxy-phenyl)-pyridine-5-carboxylate of melting point 225° C.

EXAMPLE 7

6-Phthalimido-hexyl 1,4-dihydro-2,6-dimethyl-3-nitro-4-(2-benzyloxy-phenyl)-pyridine-5-carboxylate of melting point 224° C.

EXAMPLE 8

5-Phthalimido-pentyl 1,4-dihydro-2,6-dimethyl-3-nitro-4-(2-benzyloxy-phenyl)-pyridine-5-carboxylate of melting point 164° C.

EXAMPLE 9

β-Acetoxy-ethyl 1,4-dihydro-2,6-dimethyl-3-nitro-4-[2-(4-methyl-benzyloxy)-phenyl]-pyridine-5-thiocarboxylate of melting point 135°–137° C.

EXAMPLE 10

β-Acetoxy-ethyl 1,4-dihydro-2,6-dimethyl-3-nitro-4-(2-fluorophenyl)-pyridine-5-thiocarboxylate, isolated as a foam, Rf value 0.45.

Unless expressly indicated otherwise, these and all the following Rf values are determined on: thin layer chromatography aluminum roll, Merck, silica gel 60 F254; eluant: toluene: ethyl acetate (1:1 by volume).

EXAMPLE 11

β-Acetylthio-ethyl 1,4-dihydro-2,6-dimethyl-3-nitro-4-(2-nitrophenyl)-pyridine-5-carboxylate, isolated as a foam. Rf value: 0.30.

EXAMPLE 12

β-Acetylthio-ethyl 1,4-dihydro-2,6-dimethyl-3-nitro-4-(2-fluorophenyl)-pyridine-5-carboxylate of melting point 140°–143° C.

EXAMPLE 13

β-Acetoxy-ethyl 1,4-dihydro-2,6-dimethyl-3-nitro-4-(2-chlorophenyl)-pyridine-5-thiocarboxylate, isolated as a foam.
Rf value 0.364.

EXAMPLE 14

β-Acetoxy-ethyl 1,4-dihydro-2,6-dimethyl-3-nitro-4-(4-chlorophenyl)-pyridine-5-thiocarboxylate, isolated as a foam, Rf value: 0.386.

EXAMPLE 15

β-Acetoxyethyl 1,4-dihydro-2,6-dimethyl-3-nitro-4-(3-chlorophenyl)-pyridine-5-carboxylate of melting point 122°–124° C.

EXAMPLE 16

β-Acetoxyethyl 1,4-dihydro-2,6-dimethyl-3-nitro-4-(2-fluorophenyl)-pyridine-5-carboxylate of melting point 182°–184° C.

EXAMPLE 17

Process variant D

β-Hydroxy-ethyl 1,4-dihydro-2,6-dimethyl-3-nitro-4-(2-chlorophenyl)-pyridine-5-thiocarboxylate 3 g of 1,4-dihydro-2,6-dimethyl-3-nitro-4-(2-chlorophenyl)-pyridine-5-carboxylic acid imidazolide are boiled in 12.5 ml of absolute tetrahydrofuran with 5 ml of mercaptoethanol for 7 hours. The mixture is concentrated, the concentrate is concentrated at 70° C. using an oil pump, the residue is dissolved in chloroform and the solution is washed twice with water, dried and concentrated. The resulting evaporation residue is purified over a silica gel column with a volume of 160 ml, using toluene and later toluene/ethyl acetate 6:1 as the mobile phase. 1.94 g of a yellow foam with an Rf value of 0.25 are obtained as the main fraction.

The by-product isolated is

EXAMPLE 18

β-Mercaptoethyl 1,4-dihydro-2,6-dimethyl-3-nitro-4-(2-chlorophenyl)-pyridine-5-carboxylate of Rf value 0.55.

The following compounds are obtained analogously to Example 17:

EXAMPLE 19

β-Mercaptoethyl 1,4-dihydro-2,6-dimethyl-3-nitro-4-(3-chlorophenyl)-pyridine-5-carboxylate of Rf value 0.54.

EXAMPLE 20

β-Hydroxy-ethyl 1,4-dihydro-2,6-dimethyl-3-nitro-4-(3-chlorophenyl)-pyridine-5-thiocarboxylate of Rf value 0.24.

EXAMPLE 21

β-Hydroxy-ethyl 1,4-dihydro-2,6-dimethyl-3-nitro-4-(2-fluorophenyl)-pyridine-5-thiocarboxylate of Rf value 0.25.

EXAMPLE 22

β-Hydroxy-ethyl 1,4-dihydro-2,6-dimethyl-3-nitro-4-[2-(4-chloro-benzyloxy)-phenyl]-pyridine-5-thiocarboxylate of melting point 186° C.

EXAMPLE 23

β-Hydroxy-ethyl 1,4-dihydro-2,6-dimethyl-3-nitro-4-phenyl-pyridine-5-thiocarboxylate, isolated as an oil of Rf value 0.21.

EXAMPLE 24

β-Hydroxy-ethyl 1,4-dihydro-2,6-dimethyl-3-nitro-4-[2-(4-methyl-benzyloxy)-phenyl]-pyridine-5-thiocarboxylate of melting point 186°–190° C.

EXAMPLE 25

Process variant E

β-Hydroxyethyl 1,4-dihydro-2,6-dimethyl-3-nitro-4-(2-benzyloxyphenyl)-pyridine-5-carboxylate

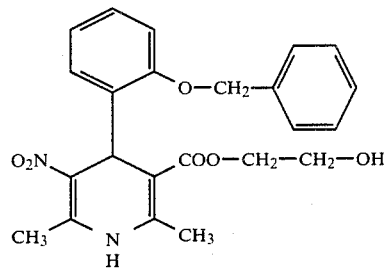

1 g of β-acetoxy-ethyl 1,4-dihydro-2,6-dimethyl-3-nitro-4-(2-benzyloxyphenyl)-pyridine-5-carboxylate is suspended in 120 ml of absolute methanol, and 2 ml of 1 molar sodium methylate solution are added, a dark red solution soon being formed. When the reaction has ended (check by thin layer chromatography), the mixture is rendered neutral with Amberlite IR 120 H⊕ and filtered and the filtrate is concentrated. The solid evaporation residue is stirred with ethanol and filtered off with suction. 600 mg (65.8% of theory) of a yellow-colored compound of melting point 183°–185° C. are obtained.

The following compounds are prepared analogously to Example 25:

EXAMPLE 26

β-Hydroxy-ethyl 1,4-dihydro-2,6-dimethyl-3-nitro-4-phenyl-pyridine-5-carboxylate of melting point 170°–172° C.

EXAMPLE 27

β-Hydroxy-ethyl 1,4-dihydro-2,6-dimethyl-3-nitro-4-(2-chlorophenyl)-pyridine-5-carboxylate of melting point 96° C.

EXAMPLE 28

β-Hydroxy-ethyl 1,4-dihydro-2,6-dimethyl-3-nitro-4-(3-chlorophenyl)-pyridine-5-carboxylate of melting point 168° C.

EXAMPLE 29

Process variant D

β-Hydroxyethyl 1,4-dihydro-2,6-dimethyl-3-nitro-4-[2-(4-chlorobenzyloxy)-phenyl]-pyridine-5-carboxylate

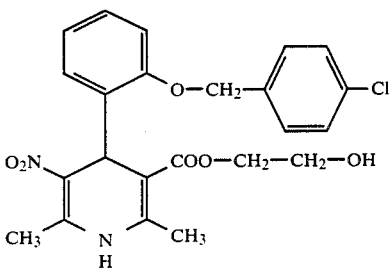

3 g of 1,4-dihydro-2,6-dimethyl-3-nitro-4-[2-(4-chlorobenzyloxy)-phenyl]-pyridine-5-carboxylic acid imidazolide are stirred in 75 ml of ethylene glycol at 140° C. for 2 hours. The mixture is cooled and taken up in ethyl acetate/water and the phases are separated. The aqueous phase is extracted with ethyl acetate and the combined ethyl acetate phases are washed several times with water, dried and concentrated. The solid evaporation residue is recrystallized from acetonitrile. 1.3 g of yellow-colored crystals of melting point 204°–207° C. are obtained.

The following compounds are prepared analogously:

EXAMPLE 30

β-Hydroxyethyl 1,4-dihydro-2,6-dimethyl-3-nitro-4-(3-nitrophenyl)-pyridine-5-carboxylate of melting point 200° C.

EXAMPLE 31

β-Hydroxyethyl 1,4-dihydro-2,6-dimethyl-3-nitro-4-(2-fluorophenyl)-pyridine-5-carboxylate, isolated as a foam of Rf value 0.16.

EXAMPLE 32

β-Hydroxyethyl 1,4-dihydro-2,6-dimethyl-3-nitro-4-[2-(4-methyl-benzyloxy)-phenyl]-pyridine-5-carboxylate of melting point 193°–194° C.

EXAMPLE 33

β-Hydroxyethyl 1,4-dihydro-2,6-dimethyl-3-nitro-4-(2-nitrophenyl)-pyridine-5-carboxylate of melting point 154° C.

EXAMPLE 34

β-Hydroxyethyl 1,4-dihydro-2,6-dimethyl-3-nitro-4-(2-methylphenyl)-pyridine-5-carboxylate of melting point 125° C.

Preparation EXAMPLE No. 35

(Process variant F)

β-Acetoxyethyl 1,4-dihydro-2,6-dimethyl-3-nitro-4-(2-chlorophenyl)-pyridine-5-carboxylate 1 g of β-hydroxyethyl 1,4-dihydro-2,6-dimethyl-3-nitro-4-(2-chlorophenyl)-pyridine-5-carboxylate is stirred overnight in a mixture of 15 ml of pyridine and 15 ml of acetic anhydride. The mixture is poured into water and extracted with ethyl acetate and the extract is washed with 1 N HCl, water, sodium bicarbonate solution and water again, dried and concentrated. The evaporation residue is crystallized with ethanol, filtered off with suction and washed with ethanol. 800 mg of a yellow-coloured compound of melting point 166° C. which is identical to the compound from Preparation Example 1, process variant A are obtained.

The following compounds are prepared analogously:

EXAMPLE 36

5-Acetylamino-pentyl 1,4-dihydro-2,6-dimethyl-3-nitro-4-(2-benzyloxyphenyl)-pyridine-5-carboxylate of melting point 191° C.

EXAMPLE 37

β-Acetylaminoethyl 1,4-dihydro-2,6-dimethyl-3-nitro-4-(2-benzyloxyphenyl)-pyridine-5-carboxylate of melting point 252° C.

Preparation Example 38

(Process variant E)

β-Aminoethyl 1,4-dihydro-2,6-dimethyl-3-nitro-4-(2-benzyloxyphenyl)-pyridine-5-carboxylate

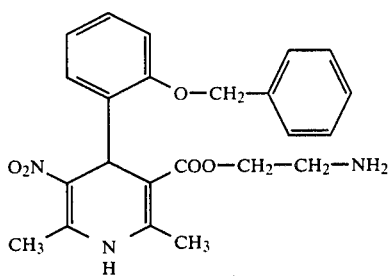

14.5 g (26.22 mmol) of β-phthalimido-ethyl 1,4-dihydro-2,6-dimethyl-3-nitro-4-(2-benzoyloxyphenyl)-pyridine-5-carboxylate are suspended in 260 ml of ethanol, and 7 ml (140 mmol) of hydrazine hydrate in 20 ml of ethanol are added dropwise, while boiling. The mixture is boiled for 2 hours, cooled and filtered with suction. The resulting solid product is stirred with 200 mmol of 0.5 N sodium hydroxide solution for 30 minutes, filtered off with suction, washed with water and ethanol and dried. 9.5 g of crystals which are red-orange in color and have a melting point of 216° C. are obtained.

The following compounds are prepared analogously:

EXAMPLE 39

6-Aminohexyl 1,4-dihydro-2,6-dimethyl-3-nitro-4-(2-benzyloxy-phenyl)-pyridine-5-carboxylate of melting point 146° C.

EXAMPLE 40

5-Amino-pentyl 1,4-dihydro-2,6-dimethyl-3-nitro-4-(2-benzyloxy-phenyl)-pyridine-5-carboxylate of melting point 148° C.

EXAMPLE 41

Process variant C

Ethoxycarbonylethyl-mercaptoethyl 1,4-dihydro-2,6-dimethyl-3-nitro-4-(2-benzyloxy-phenyl)-pyridine-5-carboxylate

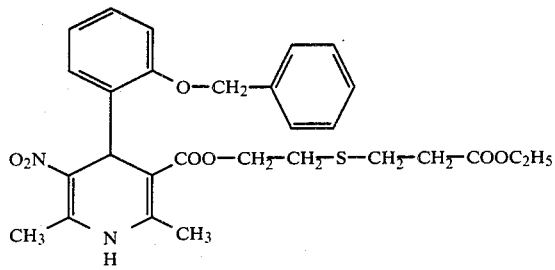

12 g (40 mmol) of 2-benzyloxybenzylidene-nitroacetone are boiled with 10.5 g of ethoxycarbonyl-ethylmercapto β-aminocrotonate in 80 ml of ethanol for 4 hours. The mixture is concentrated and the residue is purified over a silica gel column with toluene/ethyl acetate in a volume ratio of 10:1. The fractions containing the clean product are combined and concentrated. After recrystallization from ethanol, 10.2 g of orange-colored crystals of melting point 133° C. are obtained.

EXAMPLE 42

Ethoxycarbonylpropyl-mercaptoethyl 1,4-dihydro-2,6-dimethyl-3-nitro-4-(2-benzyloxy-phenyl)-pyridine-5-carboxylate of melting point 121° C.

Hydrolysis of the compound from Example 41 gives:

EXAMPLE 43

Hydroxycarbonylethylmercaptoethyl 1,4-dihydro-2,6-dimethyl-3-nitro-4-(2-benzyloxy-phenyl)-pyridine-5-carboxylate of melting point 178° C.

EXAMPLE 44

(from Example 42)

Hydroxycarbonyl-propylmercaptoethyl 1,4-dihydro-2,6-dimethyl-3-nitro-4-(2-benzyloxy-phenyl)-pyridine-5-carboxylate of melting point 160° C.

EXAMPLE 45

Process variant G (2-(2-Acetylthio-ethoxy)-ethyl 1,4-dihydro-2,6-dimethyl-3-nitro-4-(2-benzyloxy-phenyl)-pyridine-5-carboxylate

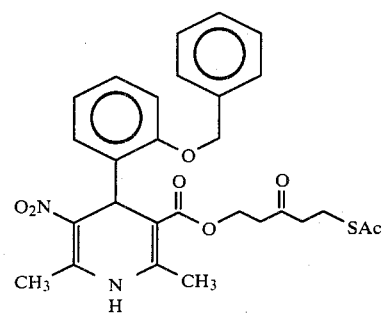

1.3 g of 2-(2-chloroethoxy)-ethyl 1,4-dihydro-2,6-dimethyl-3-nitro-4-(2-benzyloxyphenyl)-pyridine-5-carboxylate are dissolved in 15 ml of dimethylformamide and, after addition of 500 mg of potassium thioacetate, the mixture is stirred overnight at 100° C. When the reaction has ended, the mixture is concentrated via a rotary evaporator, the residue is taken up in chloroform and the organic phase is washed with water, dried and concentrated. The crystalline residue is recrystallized from ethyl acetate/petroleum ether.

Yield: 1.1 g (78%).
melting point: 167° C.
Rf (toluene/acetone 4:1): 0.46.
Rf (toluene/ethyl acetate (EA) 6:1): 0.39.

The following compounds are prepared analogously:

EXAMPLE 46

(4-Acetylthio)butyl 1,4-dihydro-2,6-dimethyl-3-nitro-4-(2-benzyloxy-phenyl)-pyridine-5-carboxylate Rf (toluene/acetone 4:1): 0.48.
Rf (toluene/EA 6:1): 0.39.

EXAMPLE 47

(6-Acetylthio)hexyl 1,4-dihydro-2,6-dimethyl-3-nitro-4-(2-benzyloxy-phenyl)-pyridine-5-carboxylate Rf (toluene/acetone 4:1): 0.54.
Rf (toluene/EA 6:1): 0.41.

EXAMPLE 48

(8-Acetylthio-3,6-dioxo)-octyl 1,4-dihydro-2,6-dimethyl-3-nitro-4-(2-benzyloxy-phenyl)-pyridine-5-carboxylate Rf (toluene/acetone 4:1): 0.42.
Rf (toluene/EA 6:1): 0.39.

EXAMPLE 49

(Preparation according to process variant G)

(11-Acetylthio)-undecyl 1,4-dihydro-2,6-dimethyl-3-nitro-4-(2-benzyloxy-phenyl)-pyridine-5-carboxylate Rf (toluene/acetone 4:1): 0.59.
Rf (toluene/EA 6:1): 0.43.

EXAMPLE 50

(2-Dimethylaminoethylmercapto)-ethyl 1,4-dihydro-2,6-dimethyl-3-nitro-4-(2-benzyloxy-phenyl)-pyridine-5-carboxylate of melting point 125° C.

(Rf value, thin layer chromatography aluminium roll, Merck, silica gel 60 F 254, eluant: chloroform/methanol in a volume ratio of 3:1).

Rf value: 0.66.

EXAMPLE 51

(3-Dimethylaminoethylmercapto)-propyl 1,4-dihydro-2,6-dimethyl-3-nitro-4-(2-benzyloxy-phenyl)-pyridine-5-carboxylate of melting point 127° C.

(Rf value, thin layer chromatography aluminum roll, Merck, silica gel 60 F 254, eluant: chloroform/methanol in a volume ratio of 3:1).

Rf value: 0.43.

EXAMPLE 52

3-Acetylmercaptopropyl 1,4-dihydro-2,6-dimethyl-3-nitro-4-(3-chlorophenyl)-pyridine-5-carboxylate of melting point 125°–127° C.

EXAMPLE 53

3-Acetylmercaptopropyl 1,4-dihydro-2,6-dimethyl-3-nitro-4(2-fluorophenyl)-pyridine-5-carboxylate of melting point 125°–130° C.

EXAMPLE 54

β-Acetylmercaptoethyl 1,4-dihydro-2,6-dimethyl-3-nitro-4-(3-chlorophenyl)-pyridine-5-carboxylate of melting point 102°–104° C.

EXAMPLE 55

β-Acetylmercaptoethyl 1,4-dihydro-2,6-dimethyl-3-nitro-4-(3-methylphenyl)-pyridine-5-carboxylate of melting point 150° C.

EXAMPLE 56

3-Acetylmercaptopropyl 1,4-dihydro-2,6-dimethyl-3-nitro-4-(3-methylphenyl)-pyridine-5-carboxylate of melting point 184° C.

EXAMPLE 57

3-Acetylmercaptopropyl 1,4-dihydro-2,6-dimethyl-3-nitro-4-(2-chlorophenyl)-pyridine-5-carboxylate of melting point 197° C.

EXAMPLE 58

β-Acetylmercaptoethyl 1,4-dihydro-2,6-dimethyl-3-nitro-4-(2-methylphenyl)-pyridine-5-carboxylate of melting point 180° C.

EXAMPLE 59

β-Acetylmercaptoethyl 1,4-dihydro-2,6-dimethyl-3-nitro-4-(2,3-dichlorophenyl)-pyridine-5-carboxylate

EXAMPLE 60

3-Acetylmercaptopropyl 1,4-dihydro-2,6-dimethyl-3-nitro-4-(2,3-dichlorophenyl)-pyridine-5-carboxylate

EXAMPLE 61

3-Mercaptopropyl 1,4-dihydro-2,6-dimethyl-3-nitro-4-(3-chlorophenyl)-pyridine-5-carboxylate
Rf value = 0.5.

Thin layer chromatography aluminum roll, Merck, silica gel 60 F 254: eluant chloroform/ethyl acetate in a volume ratio of 6:1.

EXAMPLE 62

3-Mercaptopropyl 1,4-dihydro-2,6-dimethyl-3-nitro-4-(2-fluorophenyl)-pyridine-5-carboxylate of Rf value 0.5.

EXAMPLE 63

β-Mercaptoethyl 1,4-dihydro-2,6-dimethyl-3-nitro-4-(3-methylphenyl)-pyridine-5-carboxylate of Rf value 0.49.

EXAMPLE 64

3-Mercaptopropyl 1,4-dihydro-2,6-dimethyl-3-nitro-4-(3-methylphenyl)-pyridine-5-carboxylate of Rf value 0.49.

EXAMPLE 65

3-Mercaptopropyl 1,4-dihydro-2,6-dimethyl-3-nitro-4-(2-chlorophenyl)-pyridine-5-carboxylate of Rf value 0.46.

EXAMPLE 66

2-Mercaptoethyl 1,4-dihydro-2,6-dimethyl-3-nitro-4-(2-methylphenyl)-pyridine-5-carboxylate of Rf value 0.52.

EXAMPLE 67

2-Mercaptoethyl 1,4-dihydro-2,6-dimethyl-3-nitro-4-(2,3-dichlorophenyl)-pyridine-5-carboxylate.

EXAMPLE 68

3-Mercaptopropyl 1,4-dihydro-2,6-dimethyl-3-nitro-4-(2,3-dichlorophenyl)-pyridine-5-carboxylate.

It will be understood that the specification and examples are illustrative but not limitative of the present invention and that other embodiments within the spirit and scope of the invention will suggest themselves to those skilled in the art.

What is claimed is:

1. A 3-nitro-dihydropyridine derivative of the formula

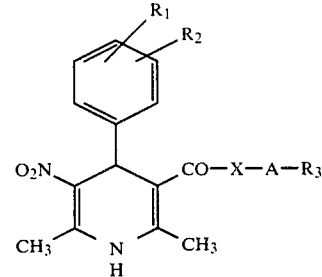

in which
$R_1$ and $R_2$ each independently is hydrogen, $C_1$–$C_4$-alkyl, $C_1$–$C_{12}$-alkoxy, $C_1$–$C_4$-halogenoalkoxy, halogen, nitro, $C_1$–$C_4$-halogenoalkyl, $C_1$–$C_4$-halogenoalkylmercapto,

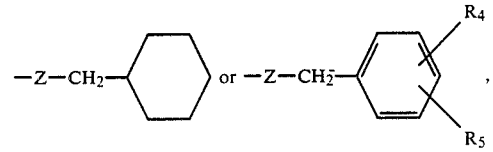

Z is oxygen or sulphur,
$R_4$ and $R_5$ each independently is hydrogen, $C_1$–$C_4$-alkyl, $C_1$–$C_6$-alkoxy, halogen, $C_1$–$C_4$-halogenoalkyl, $C_1$–$C_4$-halogenoalkoxy or nitro, or
$R_1$ and $R_2$, together with 2 C atoms of the phenyl ring form the ring

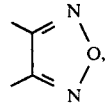

X is oxygen or sulphur,
A is a hydrocarbon radical with up to 12 C atoms which optionally contains one or two identical or different chain members from the group consisting of O, S and CO and/or which is optionally substituted by hydroxyl or aliphatic acyloxy with up to 4 C atoms, $R_3$ is —O—$COR_6$, —S—CO—$R_6$, SH,

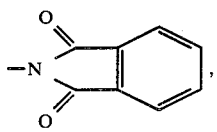

NH—$COR_6$, $COOR_6$, or $CONR_7R_8$, $R_6$ is hydrogen or an aliphatic radical with up to 6 C atoms or a phenyl radical, and $R_7$ and $R_8$ each independently is hydrogen or an aliphatic radical with up to 6 C atoms or a phenyl radical, or a physiologically acceptable salt thereof.

2. A compound or salt according to claim 1, in which
$R_1$ is hydrogen,
$R_2$ is halogen, trifluoromethyl, nitro, hydrogen, $C_1$–$C_4$-alkyl or one of the groups

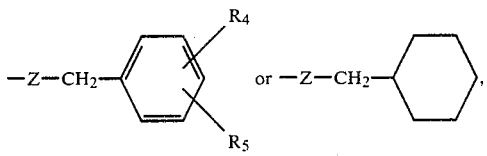

$R_3$ is $OCOR_6$, S—$COR_6$, SH, $COOR_6$, NH—$COR_6$ or —CO—$NR_7R_8$,
A is a $C_2$–$C_8$-alkyl group, and
$R_6$, $R_7$ and $R_8$ each independently is a $C_1$–$C_3$-alkyl radical.

3. A compound or salt according to claim 1, in which
$R_1$ is hydrogen,
$R_2$ is halogen, trifluoromethyl, nitro, hydrogen,

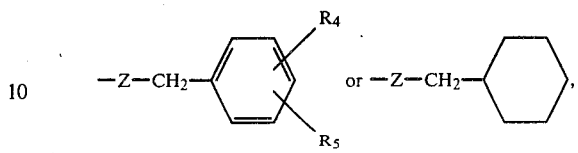

$R_3$ is $OCOR_6$, S—$COR_6$ or SH,
A is a $C_2$–$C_8$-alkyl group, and
$R_6$ is a $C_1$–$C_3$-alkyl radical.

4. A compound or salt according to claim 1, in which $R_3$ is SH.

5. A compound or salt according to claim 4, in which X is sulphur.

6. A compound or salt according to claim 1, in which X is sulphur.

7. A composition exhibiting a positive inotropic activity comprising an amount effective therefor of a compound or salt according to claim 1 in admixture with a diluent.

8. A unit dose of a composition according to claim 7 in the form of a tablet, capsule or ampule.

9. A method of increasing the contractility of the heart muscle of a patient in need thereof which comprises administering to such patient an amount effective therefor of a compound or salt according to claim 1.

* * * * *